United States Patent
Trim et al.

(10) Patent No.: US 10,832,643 B1
(45) Date of Patent: Nov. 10, 2020

(54) DYNAMIC BEAT OPTIMIZATION

(71) Applicant: International Business Machines Corporation, Armonk, NY (US)

(72) Inventors: Craig M. Trim, Ventura, CA (US); Martin G. Keen, Cary, NC (US); Michael Bender, Rye Brook, NJ (US); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/445,735

(22) Filed: Jun. 19, 2019

(51) Int. Cl.
| | |
|---|---|
| *G10H 1/00* | (2006.01) |
| *G10G 1/00* | (2006.01) |
| *H04L 29/08* | (2006.01) |
| *A61B 5/11* | (2006.01) |
| *G06N 20/00* | (2019.01) |

(52) U.S. Cl.
CPC ......... *G10H 1/0066* (2013.01); *A61B 5/1127* (2013.01); *G06N 20/00* (2019.01); *G10G 1/00* (2013.01); *H04L 67/22* (2013.01); *G10H 2220/371* (2013.01)

(58) Field of Classification Search
CPC ........... G10H 1/0066; G10H 2220/371; H04L 67/22; G10G 1/00; A61B 5/1127; G06N 20/00
See application file for complete search history.

(56) References Cited

U.S. PATENT DOCUMENTS

| | | | | |
|---|---|---|---|---|
| 5,592,143 | A * | 1/1997 | Romney | G04F 5/025 340/309.16 |
| 6,230,047 | B1* | 5/2001 | McHugh | A61B 5/024 600/519 |
| 8,952,233 | B1* | 2/2015 | Johnson | G10H 1/40 84/652 |
| 9,235,198 | B2* | 1/2016 | Caskey | G05B 1/01 |
| 2007/0113726 | A1* | 5/2007 | Oliver | A61B 5/0245 84/615 |
| 2015/0182149 | A1* | 7/2015 | Rapoport | A61B 5/1123 702/19 |
| 2015/0297109 | A1 | 10/2015 | Garten et al. | |
| 2016/0055420 | A1 | 2/2016 | Karanam et al. | |
| 2018/0314959 | A1 | 11/2018 | Apokatanidis et al. | |

OTHER PUBLICATIONS

Frank Desmet et al., "Statistical analysis of human body movement and group interactions in response to music", IPEM, Department of Musicology, Ghent University, Belgium, Jul. 31, 2009, 10 pages.

(Continued)

*Primary Examiner* — Jeffrey Donels
(74) *Attorney, Agent, or Firm* — William H. Hartwell; Hunter E. Webb; Keohane & D'Alessandro, PLLC

(57) ABSTRACT

Aspects of the present invention provide an approach for dynamically optimizing a beat. In an embodiment, a current movement rate and biometric data for each user in a group performing a physical activity are collected. An upcoming movement rate for each user is predicted based on the collected current movement rates and biometric data. Music having an optimized beat is then generated based on a lowest upcoming movement rate among the predicted upcoming movement rates.

20 Claims, 3 Drawing Sheets

(56) References Cited

OTHER PUBLICATIONS

Wendy Bumgardner, verywell fit, "Favorite Walking Music Mixes and Playlists", Move to the Beat, https://www.verywellfit.com/walking-music-mix-playlist-workout-songs-3435845, May 30, 2018, 5 pages.

Chris Welch, The Verge, "Spotify will match music to your running pace", https://www.theverge.com/2015/5/20/8630213/spotify-unveils-new-design-for-runners, May 20, 2015, 2 pages.

Lori A. Selke, "Good Walking Music", https://www.livestrong.com/article/168496-list-of-good-walking-music/, Copyright 2019 Leaf Group Ltd., 11 pages.

Sonja Puzic, "Instantaneous results: How music transformed a man with Parkinson's", https://www.ctvnews.ca/health/instantaneous-results-how-music-transformed-a-man-with Parkinson's, https://www.ctvnews.ca/health/instantaneous-results-how-music-transformed-a-man-with-parkinson-s-1.3248622, Jan. 19, 2017, 3 pages.

Bartu Kaleagasi, "A New AI Can Write Music as Well as a Human Composer", https://futurism.com/a-new-ai-can-write-music-as-well-as-a-human-composer, Mar. 9, 2017, 7 pages.

Rhodri Marsden, The National, "Artificial intelligence and the the future of music composition", https://www.thenational.ae/arts-culture/music/artificial-intelligence-and-the-the-future-of-music-composition-1.732554, May 21, 2018, 6 pages.

\* cited by examiner

DYNAMIC BEAT OPTIMIZATION

TECHNICAL FIELD

The subject matter of this invention relates generally to computational creativity, and more specifically to music generation and beat optimization, applications of computational creativity in the music domain.

BACKGROUND

In the field of computational creativity, music generation systems analyze existing music written by human composers and, utilizing cognitive technologies, generate novel musical compositions for performance by either human musicians or by computers. For example, IBM Watson Beat is a music generation system that utilizes neural networks to transform a simple melody and a set of parameters for a creativity engine into a fully realized musical composition (IBM is a registered trademark and Watson Beat is a trademark of International Business Machines Corporation). The set of parameters for the creativity engine can include chord progression complexity, time signature, tempo (e.g. in beats per minute), and desired energy level, amongst other things.

When music is used during physical activity, it can have work-enhancing and psychological effects. Listening to music during physical activity can both delay fatigue and lessen the subjective perception of fatigue. It can increase physical capacity, improve energy efficiency, and influence mood.

Musical rhythm can help an individual perform an activity at a certain pace as people naturally want to stay in time with a musical beat.

SUMMARY

In general, aspects of the present invention provide an approach for dynamically generating music. In an embodiment, a current movement rate and biometric data for each user in a group performing a physical activity are collected. An upcoming movement rate for each user is predicted based on the collected current movement rates and biometric data. Music having an optimized beat is then generated for the members of a group performing the physical activity to synchronize a pace of the members.

One aspect of the invention provides a computer-implemented method for dynamically generating music, comprising: capturing a current movement rate and biometric data for each user among the plurality of users performing a physical activity; predicting, based on the current movement rate and biometric data, an upcoming movement rate for each user; and generating, using a music generation system, music having an optimized beat based on a lowest upcoming movement rate among the predicted upcoming movement rates for use during the physical activity.

Another aspect of the invention provides a system for dynamically generating music, comprising: a memory medium comprising program instructions; a bus coupled to the memory medium; and a processor, for executing the program instructions, coupled to a music generation engine via the bus that when executing the program instructions causes the system to: capture a current movement rate and biometric data for each user among the plurality of users performing a physical activity; predict, based on the current movement rate and biometric data, an upcoming movement rate for each user; and generate, using a music generation system, music having an optimized beat based on a lowest upcoming movement rate among the predicted upcoming movement rates for use during the physical activity.

Yet another aspect of the invention provides a computer program product embodied in a computer readable medium that, when executed by a computer device, performs a method for dynamically generating music, the method comprising: capturing a current movement rate and biometric data for each user among the plurality of users performing a physical activity; predicting, based on the current movement rate and biometric data, an upcoming movement rate for each user; and generating, using a music generation system, music having an optimized beat based on a lowest upcoming movement rate among the predicted upcoming movement rates for use during the physical activity.

Still yet, any of the components of the present invention could be deployed, managed, serviced, etc., by a service provider who offers to implement passive monitoring in a computer system.

Embodiments of the present invention also provide related systems, methods, and/or program products.

BRIEF DESCRIPTION OF THE DRAWINGS

These and other features of this invention will be more readily understood from the following detailed description of the various aspects of the invention taken in conjunction with the accompanying drawings in which.

Figure 1:
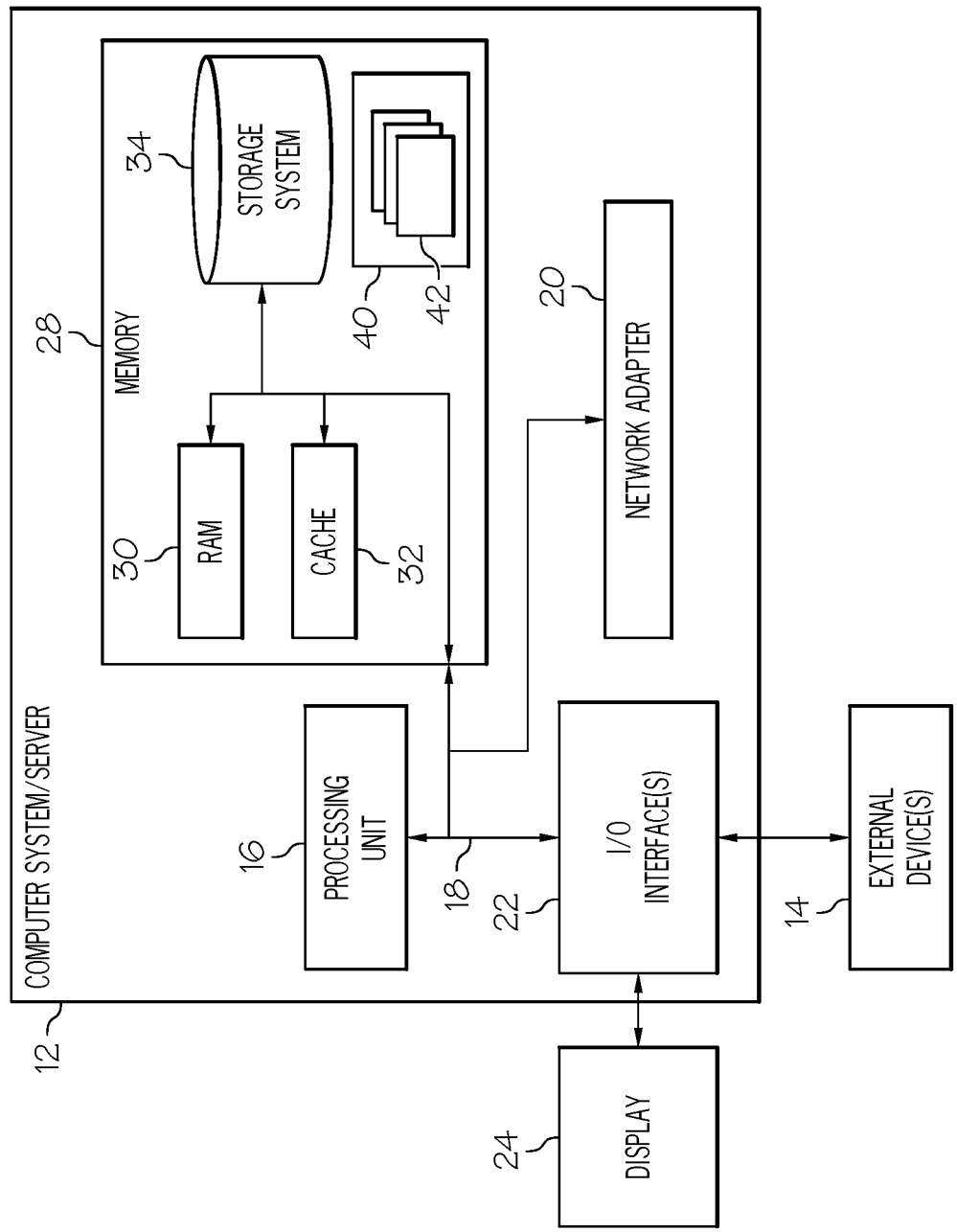
FIG. 1 depicts a data processing system according to an embodiment of the present invention.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

Illustrative embodiments will now be described more fully herein with reference to the accompanying drawings, in which embodiments are shown. This disclosure may, however, be embodied in many different forms and should not be construed as limited to the embodiments set forth herein. Rather, these embodiments are provided so that this disclosure will be thorough and complete and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The term "set" is intended to mean a quantity of at least one. It will be further understood that the terms "comprises" and/or "comprising", or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

As indicated above, aspects of the present invention provide an approach for dynamically generating music. In an embodiment, a current movement rate and biometric data for each user in a group performing a physical activity are collected. An upcoming movement rate for each user is predicted based on the collected current movement rates and biometric data. Music having an optimized beat is then generated for the members of a group performing the physical activity to synchronize a pace of the members.

Referring now to FIG. 1, a schematic of an example of a data processing system is shown. Data processing system 10 is only one example of a suitable data processing system and is not intended to suggest any limitation as to the scope of use or functionality of embodiments of the invention described herein. Regardless, data processing system 10 is capable of being implemented and/or performing any of the functionality set forth hereinabove.

In data processing system 10, there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on, that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in data processing system 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM, or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program code embodied on a computer readable medium may be transmitted using any appropriate medium including, but not limited to, wireless, wireline, optical fiber cable, radio-frequency (RF), etc., or any suitable combination of the foregoing.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a consumer to interact with computer system/server 12; and/or any devices (e.g., network card, modem, etc.) that enable computer system/server 12 to communicate with one or more other computing devices. Such communication can occur via I/O interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
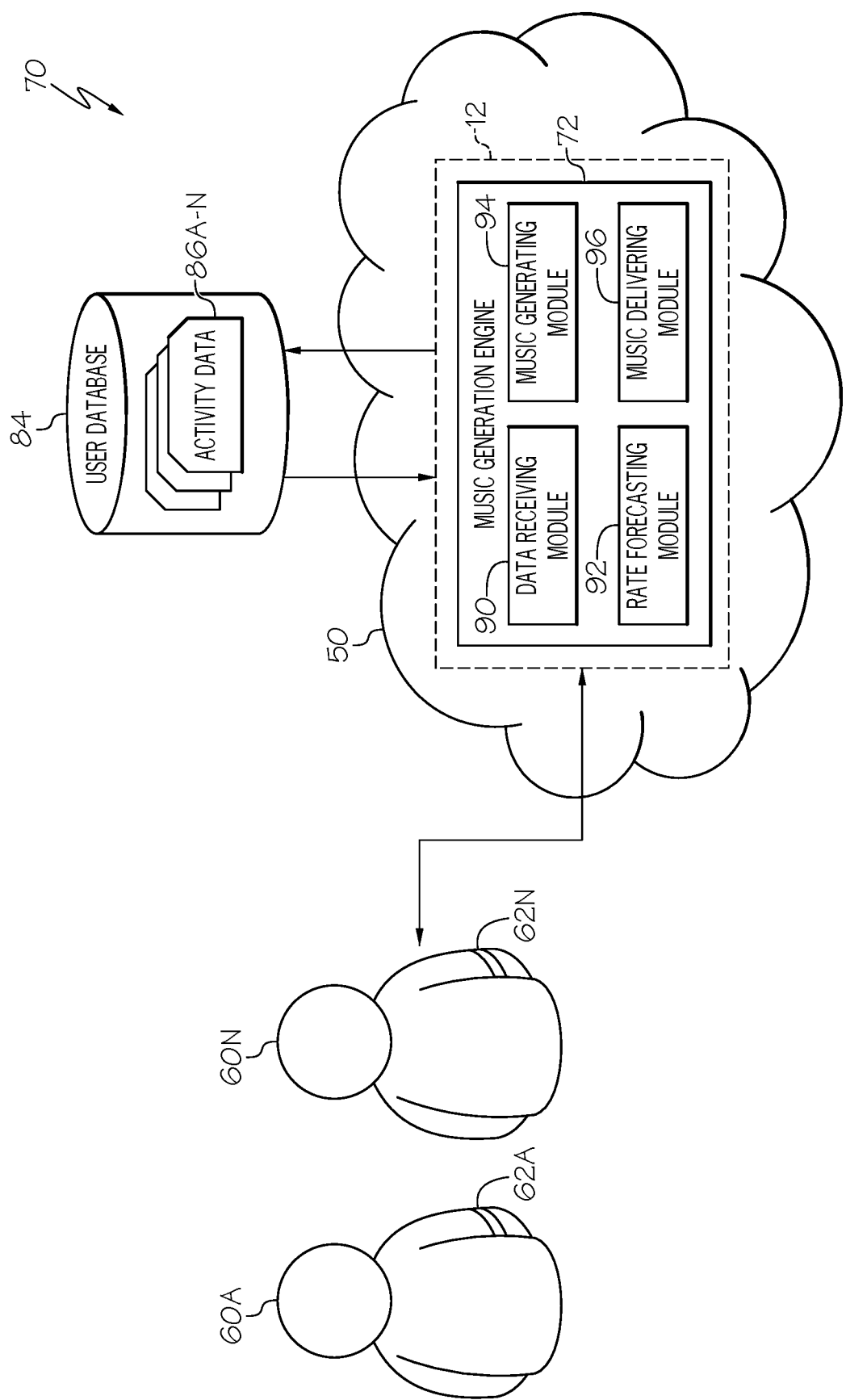
FIG. 2 depicts a system diagram according to an embodiment of the present invention.

Referring now to FIG. 2, a system diagram describing the functionality discussed herein according to an embodiment of the present invention is shown. It is understood that the teachings recited herein may be practiced within any type of networked computing environment 70 (e.g., a cloud computing environment 50). A stand-alone computer system/server 12 is shown in FIG. 2 for illustrative purposes only. In the event the teachings recited herein are practiced in a networked computing environment 70, each equipped user 60 need not have a music generation engine (hereinafter "system 72"). Rather, system 72 could be loaded on a server or server-capable device that communicates (e.g., wirelessly) with users 60A-N to provide processing therefor. Regardless, as depicted, system 72 is shown within computer system/server 12. In general, system 72 can be implemented as program/utility 40 on computer system 12 of FIG. 1 and can enable the functions recited herein. It is further understood that system 72 may be incorporated within or work in conjunction with any type of system that receives, processes, and/or executes commands with respect to music generation. Such other system(s) have not been shown in FIG. 2 for brevity purposes.

Along these lines, system 72 may perform multiple functions similar to a general-purpose computer. Specifically, among other functions, system 72 can generate music having an optimized beat for a group performing a physical activity. To accomplish this, system 72 can include a data receiving module 90, a rate forecasting module 92, a music generating module 94, and a music delivering module 96.

Performing a physical activity with a group can include benefits such as enhancing consistency, duration, motivation, conversation, and inspiration. However, when multiple people are performing an activity together, their capabilities can be different, and there can be a natural frustration when some can perform the activity at a different pace than the others. When music is used during physical activity, it can have work-enhancing and psychological effects. Listening to music during physical activity can both delay fatigue and lessen the subjective perception of fatigue. It can increase physical capacity, improve energy efficiency, and influence mood. Music can be helpful in pacing group members when each are performing the same physical activity. However, music played from a radio station or predefined playlist (e.g., music played by a group fitness instructor) can have a beat or rhythm that is either too fast or too slow for some members of the group, causing some members to perform the activity out of sync with other members.

The current embodiments described herein solve these and/or other problems in the current solutions by generating music having an optimized beat for persons performing a physical activity as a group. By generating music having an optimized beat for members of a group performing a physical activity, the members are able to synchronize their pace so that they are able to perform the activity together. Since the system described herein continues to monitor each user along with additional related factors (e.g., terrain, weather, etc.), the beat can continue to change as the pace of the group members change.

Referring again to FIG. 2, data receiving module 90 of system 72, as executed by computer system/server 12, is configured to receive a current movement rate and biometric data for each user in a group performing a physical activity. Users 60A-N (singly user 60N) are shown participating in a group physical activity. As shown, the physical activity is running. However, the physical activity can include any movements performed by a group, such as cardiovascular and calisthenic exercises, for example.

Each person in the group can have any number of wearable Internet of Things (IoT) devices 62A-N (singly device 62N). A wearable IoT device can be used for tracking a user's vital signs or pieces of data related to health and fitness, location, his/her biofeedback indicating emotions, and/or the like. Persons wishing to participate in the music generation service provided by system 72 must have at least one wearable IoT device that is worn during the physical activity. As shown, user 60N wears smart watch 62N. Data cannot be collected on individuals in the group not having a participating device. Therefore, information related to those individuals will not be included for analysis when producing music at an appropriate speed and rhythm to help coordinate group movement at the appropriate speed.

In an embodiment, user 60N may be required to register the device 62N prior to data collection to enable data communications and information sharing between the device 62N and system 72. For example, user 60N may be instructed to initially pair the device 62N with a separate device (e.g., a network-connected device such as a smart phone) through which registration can be performed. In any case, a communication link (e.g., Wi-Fi, cellular, etc.) must be established between the device 62N and system 72 to enable data collection by data receiving module 90.

Each wearable IoT device (e.g., device 62N) can include any number of sensors for collecting information. Sensors can collect information related to actual movements of user 60N when performing a physical activity, how user 60N is responding to the physical activity, and/or other factors that might affect the user/activity. Example sensors for collecting movement data include a gyroscope and accelerometer. A gyroscope is used to measure angular velocity as it detects orientation and rotation. An accelerometer tracks the basic human movements in all directions, such as tilt, inclination, and the overall orientation of the body. A gyroscope is often paired with an accelerometer to give a 3D representation of a movement. These sensors can prove valuable when determining a movement rate. For example, an accelerometer and gyroscope can be used together to detect a movement rate (e.g., running or walking cadence) when part of wearable IOT device 62N.

Example sensors for collecting biometric data include wearable electrodes, temperature sensors, biochemical sensors, and optical heart rate sensors. Electric pulses in wearable electrodes read a heart rate in a person, so the electrodes are typically made to stick directly onto the skin. Electrodes in medical wearable devices measure electromyography (EMG), electroencephalogram (EEG) and electrocardiogram (EKG) on a specific part of the body. EMG measures an electrical activity of muscles. EEG measures an electrical activity in a brain. EKG measures an electrical activity in a heart.

A biochemical sensor in a wearable device can convert a chemical component in contact to an electric signal. Biochemical sensors work on the mechanism of chemiresistive detection in a wearable configuration. The electrochemical sensor configuration performs continuous monitoring of EtG (ethyl glucuronide) from a person's sweat to help keep a track of their metabolic rate. An ambient weather sensor can sense local ambient weather conditions.

An optical heart rate sensor typically consists of a photodiode and light-emitting diodes (LEDs) both on one side of the system. A person's body constantly emits biophotons. The photodiodes in the sensor capture the light present in the blood that can be used to determine an instantaneous heartbeat of the person. A temperature sensor keeps track of the body temperature; the more the body seems to heat up, the more intense a physical activity is detected by a device with this sensor.

In addition, other sensors can be used to collect location and/or environmental information that might affect a group physical activity. For example, a wearable IoT device can include global positioning system (GPS) capabilities and/or other position tracking sensors to measure a person's location and movement pattern. Another example sensor is a proximity sensor that can detect whether a defined subject is present nearby. The defined subject can vary from an actual human to non-living objects or even walls. A wearable proximity sensor can be useful in devices with applications related to obstacle detection, detection of certain objects, etc. For example, an obstacle such as a fallen tree across a running path can affect members of a group out for a run along the path. The example sensors provided above are illustrative only and not intended to be limiting. Any sensor, either now known or later developed, may be used if it provides useful information that can affect a movement rate of a user among the group performing the activity.

In an embodiment, movement rates and biometrics received by data receiving module 90 from participating wearable IoT devices 62A-N can be stored in user database 84 to create a historical corpus for individuals. User database 84 can use any type of database structure (e.g., relational, hierarchical, etc.) to store historical activity data 86A-N for users 60A-N. User database 84 can further store a user profile for each of users 60A-N. Each user profile can include information for the user such as, registered device(s), favorite music genre(s), and/or the like.

In an embodiment, data receiving module 90 is further configured to receive additional data related to a particular group session, such as type of activity (e.g., running, walking, aerobics, etc.), time of day, weather data (e.g., raining, hot, etc.), topological information of a location (e.g., flat, hills, beach, etc.), and/or the like. Data receiving module 90 may receive additional data from any number of sources, such as a participating wearable IoT device, a separate user device (e.g., calendar app, social media app, etc.), a manual user submission via an app interface, Internet sources (e.g., a weather data source, etc.), etc. Any additional data gathered can be stored in user database 84 for later analysis when forecasting an upcoming movement rate for a particular user, as described in greater detail below.

Rate forecasting module 92 of system 72, as executed by computer system/server 12, is configured to predict, using machine learning, an upcoming movement rate for each user in a group performing a physical activity. Machine learning is an application of artificial intelligence (AI) that provides systems the ability to automatically learn and improve from experience without being explicitly programmed. Machine learning focuses on the development of computer programs that can access data and use the data to learn for themselves. As such, data receiving module 90 continues to receive data (e.g., continual, every few seconds, etc.) from wearable IoT devices 62A-N as a group activity session advances and stores the data in user database 84. As stated, gathered data for each user 60A-N can be used to cognitively predict an upcoming movement rate for each user based on the user's historical capabilities. Music can then be generated with a beat that is acceptable as individual capabilities change throughout a session. By constantly analyzing the group, the generated music can be changed at any given time as opposed to using a pre-selected song or playlist that would need to finish or be interrupted.

Referring again to FIG. 2, two users (user 60A and user 60N) from a group are depicted. Assume historic and learned data for user 60N is stored in user database 84. This information, along with currently collected data, can be used for predicting an upcoming movement rate for user 60N. For example, if user 60N began performing arm circles at 60 rotations per minute for the first minute but has historically slowed down to 50 rotations per minute in the second minute, rate forecasting module 92 can predict 50 rotations per minute as user 60N enters into the second minute of a group activity involving arm rotations. Assume the group meets weekly to perform this activity and user 60N begins to get stronger as weeks pass. She is now able to perform 55 rotations per minute in the second minute. Since system 72 continues to learn, this information can be stored in user database 84 and relied upon to refine predictions going forward.

In an embodiment, rate forecasting module 92 can search for a historical scenario which resembles current conditions, as described above in reference to FIG. 2. For example, assume user 60N has historically run at 150 steps per minute on flat ground when her heart rate was between 150 and 160 beats per minute (bpm) after 5 minutes of running. If a current run presents a similar scenario (e.g., flat ground, heart rate at 155 bpm), a movement rate of 150 steps per minute at a 5 minute mark in the run can be predicted for the future rate.

In another example, assume user 60N is approaching a steep hill during her run. Historically, user 60N typically slows her cadence by 5% when going up a steep hill (e.g., greater than 40 degree incline). Therefore, the 5% decrease in movement rate can be used to derive an upcoming movement when user 60N is approaching such a hill in a current group activity session.

If a similar historical scenario is not found, then a closest match can be chosen. Additional increases or decreases can be calculated by modifiers as described above for conditions that are not in the best match. For example, consider user 60N typically has movement rates 2% lower in the evening than in the morning. Assume historical data is found matching the hill scenario above, but all historical runs collected have taken place in the morning. The current run is in the evening. In this case, a 7% decrease (i.e., 5% due to the hill and 2% because of the time of day) in cadence can be factored in when deriving an upcoming movement rate as user 60N begins climbing the hill.

Music generating module 94 of system 72, as executed by computer system/server 12, is configured to generate, based on an upcoming movement rate of a user, music having an optimized beat for the upcoming movement of the group. When multiple people are performing an activity together, their capabilities can be different, and there can be a natural frustration when some can perform the activity at a different pace than the others. In an embodiment, music generating module 94 may be implemented through the capabilities offered by IBM Watson Beat.

Music generating module 94 is configured to determine an optimized beat for a particular movement rate. To that end, the optimized beat can be calculated based on the number of movements per minute. By using a number of movements per minute value, an optimized beat can be calculated for group activities other than walking and running, such as arm rotations, jumping jacks, etc. A rhythm or beat of a movement naturally ties to a beat of music. For example, music having 60 beats per minute (or bpm) has a slow tempo, which may be appropriate for a casual pace physical activity such as walking. Alternatively, music having 180 bpm has a fast tempo, which may be appropriate for a highly intensive physical activity (e.g., fast-paced aerobics or running).

In a typical embodiment, music generating module 94 can generate music having an optimized beat based on a slowest movement rate among the individuals in the group to facilitate synchronized activity by those involved. To that end, upcoming movement rates for all members in a group are received by music generating module 94. The slowest movement rate is selected from the rates received and used to generate music having an optimized beat for the group. By using the slowest movement rate, the generated music is used to assist each group member to keep the same pace. For example, individuals out for a morning run can pace themselves by the optimized beat which can keep them running together, rather than having some members potentially run ahead or fall back.

The optimized beat can be a function of the upcoming movement rate used. For example, everyday runners generally fall between 160-170 steps per minute, while elite runners strike the ground around 180 steps per minute or higher, with some getting above 200 at their fastest speeds. Music having 150 to 180 bpm has a fast tempo, which may be appropriate for a highly intensive physical activity such as running in which even the slowest runner in a group can maintain a fast pace. If the slowest runner in the group has an upcoming movement rate of 150 steps per minute, music having 150 bpm can be generated so that each beat equates to a run step. In another example, a multiplier can be used to derive an appropriate beat. For example, a group performing a marching activity might prefer two steps per music beat.

In an embodiment, music generating module 94 can include machine learning techniques (such as the techniques utilized by IBM Watson Beat) to generate appropriate music for each user by taking into account that particular user's personal preferences. For example, music generating module 94 can determine user 60A prefers country music with a quick beat when running, while user 60B prefers up-tempo rock music. Machine learning was born from pattern recognition and the theory that computers can learn without being programmed to perform specific tasks. As new data is exposed, computers are able to independently adapt. They can learn from previous computations to produce reliable, repeatable decisions and results. In this context, profile information (e.g., favorite genres, songs, etc.), and historical data (e.g., music played during solo runs, etc.) can be used when generating music tailored to a particular individual in a group.

In an embodiment, music generating module 94 can compare the individual preferences of the members of a group to find the highest rated common genre for the group for times when the entire group will be listening to the same music. Personal preferences of a user can initially be entered into a user profile and stored in user database 84. However, music generating module 94 can learn which genres are actually the most effective for a given movement purpose (e.g., to stay steady or to push a person to speed up). The system will continue to monitor biometrics to determine when to speed up or slow down a beat.

In an embodiment, a comparison of a physical attribute of group members can be made to determine an upcoming movement rate of each member. For example, a pace of a group of users engaged in a running activity may not only be dependent on a movement rate but also on each user's stride length. Personalized music can be provided for each individual when runners have stride lengths that differ. Each user's stride (S) can be calculated using the following formula: S=distance traveled/number of steps. Stride can be calculated for different overall speeds, as a person's stride length changes depending on how fast she is moving, as determined by distance traveled over time from an IOT device. A stride length for a current movement rate can be used when determining an upcoming movement rate. The basic formula, Distance=Rate*Time, can be used when determining an upcoming movement rate. Time and distance can be assumed to be consistent for all participants, but movement rates can differ for each individual due to differing stride lengths.

As mentioned, stride length can be factored in when determining an upcoming movement rate for each user. For example, a user having one-half a stride length as another user may have an upcoming movement rate twice that of the other user in order for the two to stay in sync. The upcoming movement rate influences the beats per minute of music being generated for each user to keep the runners running together. For example, the runner having a one-half stride length of a second runner may be provided music having twice the number of beats per minute (bpm) as the music provided to the other runner in order to keep the two together.

In addition, music generating module 94 can modify the music based on an analysis of a type of activity of a group. The type of activity can be manually entered by a user in the group via an app interface, detected by one or more wearable IOT sensors, a calendar entry of a user, etc. Based on the type of activity, music generating module 94 can modify a beat and/or genre of the music. For example, music generating module 94 can generate music for low-impact activity (e.g., slow jazz) that is different than high-impact activity (e.g., up-tempo rock music).

Music delivering module 96 of system 72, as executed by computer system/server 12, is configured to deliver the generated music to one or more output devices users 60A-N configured to play music. In an embodiment, generated music may be transmitted to an app of each user configured to play music. When music is being generated based on individual preferences, each user would ideally wear headphones for listening. For example, music having a country music feel might be generated for user 60A, while pop music is generated for user 60B. It would not be ideal to have both played in an open air together. Each user should enjoy her desired music separately. In instances when common music is generated for a group, the music can be played separately by each user (e.g., via headphones) or played on a designated single device (e.g., a smart speaker) to be enjoyed by the entire group.

Figure 3:
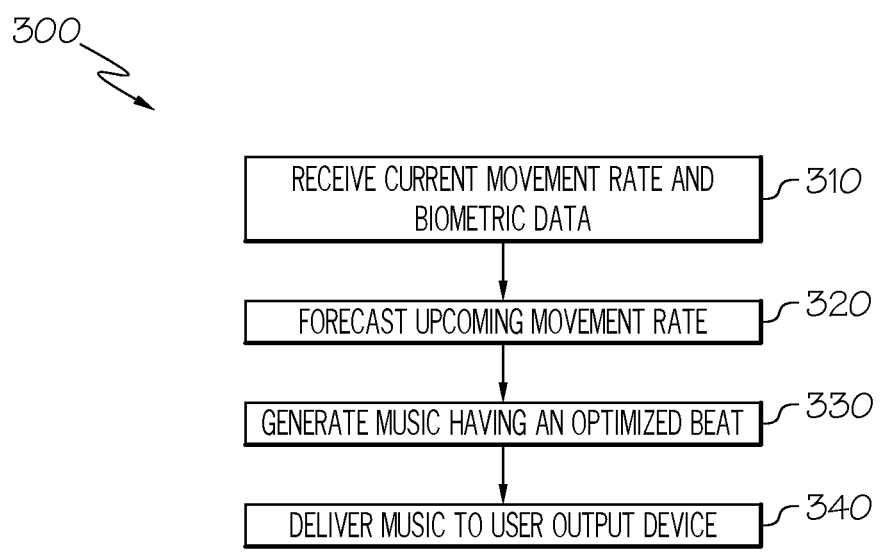
FIG. 3 depicts an example process flowchart according to an embodiment of the present invention.

Referring now to FIG. 3 in conjunction with FIG. 2, a process flowchart 500 according to an embodiment of the present invention is shown. At 310, data receiving module 90 of system 72, as executed by computer system/server 12, receives a current movement rate and biometric data for each user in a group performing a physical activity. In the running example shown in FIG. 2, a wearable IOT device having pedometer capabilities can generate the steps that a user is taking. For other movements (e.g., jumping jacks, arm rotations, etc.), an accelerometer and gyroscope can be used to determine the change in direction which will be used as the definition of movement.

At 320, rate forecasting module 92 of system 72, as executed by computer system/server 12, predicts, using machine learning, an upcoming movement rate for each user in a group performing a physical activity. As stated, data receiving module 90 continues to receive data (e.g., continual, every few seconds, etc.) from wearable IoT devices 62A-N as a group activity session advances and stores the data in user database 84. The gathered data for each user 60A-N can be used to cognitively predict an upcoming movement rate for the respective user using the user's historical capabilities.

At 330, music generating module 94 of system 72, as executed by computer system/server 12, generates, based on an upcoming movement rate of a user, music having an optimized beat for the upcoming movement of the group. When multiple people are performing an activity together, their capabilities can be different, which can cause one or more group members to perform the activity at a different pace than the others. At 340, music delivering module 96 of system 72, as executed by computer system/server 12, delivers the music to a user output device configured to play music. By outputting music having a beat optimized for the group, the members can perform the physical activity in sync with one another.

The process flowchart of FIG. 3 illustrates the architecture, functionality, and operation of possible implementations of systems, methods, and computer program products according to various embodiments of the present invention. In this regard, each block in the flowchart may represent a module, segment, or portion of code, which comprises one or more executable instructions for implementing the specified logical function(s). It should also be noted that, in some alternative implementations, the functions noted in the blocks might occur out of the order depicted in the Figures. For example, two blocks shown in succession may, in fact, be executed substantially concurrently. It will also be noted that each block of flowchart illustration can be implemented by special purpose hardware-based systems that perform the specified functions or acts, or combinations of special purpose hardware and computer instructions.

While shown and described herein as an approach for dynamically generating music, it is understood that the invention further provides various alternative embodiments. For example, in one embodiment, the invention provides a method that performs the process of the invention on a subscription, advertising, and/or fee basis. That is, a service provider, such as a Solution Integrator, could offer to provide functionality for dynamically generating music. In this case, the service provider can create, maintain, and support, etc., a computer infrastructure, such as computer system 12 (FIG. 1) that performs the processes of the invention for one or more consumers. In return, the service provider can receive payment from the consumer(s) under a subscription and/or fee agreement and/or the service provider can receive payment from the sale of advertising content to one or more third parties.

In another embodiment, the invention provides a computer-implemented method for dynamically generating music. In this case, a computer infrastructure, such as computer system 12 (FIG. 1), can be provided and one or more systems for performing the processes of the invention can be captured (e.g., created, purchased, used, modified, etc.) and deployed to the computer infrastructure. To this extent, the deployment of a system can comprise one or more of: (1) installing program code on a computing device, such as computer system 12 (FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

Some of the functional components described in this specification have been labeled as systems or units in order to more particularly emphasize their implementation independence. For example, a system or unit may be implemented as a hardware circuit comprising custom VLSI circuits or gate arrays, off-the-shelf semiconductors such as logic chips, transistors, or other discrete components. A system or unit may also be implemented in programmable hardware devices such as field programmable gate arrays, programmable array logic, programmable logic devices or the like. A system or unit may also be implemented in software for execution by various types of processors. A system or unit or component of executable code may, for instance, comprise one or more physical or logical blocks of computer instructions, which may, for instance, be organized as an object, procedure, or function. Nevertheless, the executables of an identified system or unit need not be physically located together, but may comprise disparate instructions stored in different locations which, when joined logically together, comprise the system or unit and achieve the stated purpose for the system or unit.

Further, a system or unit of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices and disparate memory devices.

Furthermore, systems/units may also be implemented as a combination of software and one or more hardware devices. For instance, system 72 may be embodied in the combination of a software executable code stored on a memory medium (e.g., memory storage device). In a further example, a system or unit may be the combination of a processor that operates on a set of operational data.

As noted above, some of the embodiments may be embodied in hardware. The hardware may be referenced as a hardware element. In general, a hardware element may refer to any hardware structures arranged to perform certain operations. In one embodiment, for example, the hardware elements may include any analog or digital electrical or electronic elements fabricated on a substrate. The fabrication may be performed using silicon-based integrated circuit (IC) techniques, such as complementary metal oxide semiconductor (CMOS), bipolar, and bipolar CMOS (BiCMOS) techniques, for example. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor devices, chips, microchips, chip sets, and so forth. However, the embodiments are not limited in this context.

Also noted above, some embodiments may be embodied in software. The software may be referenced as a software element. In general, a software element may refer to any software structures arranged to perform certain operations. In one embodiment, for example, the software elements may include program instructions and/or data adapted for execution by a hardware element, such as a processor. Program instructions may include an organized list of commands comprising words, values, or symbols arranged in a predetermined syntax that, when executed, may cause a processor to perform a corresponding set of operations.

The present invention may also be a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media/(e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

It is apparent that there has been provided approaches for dynamically generating music. While the invention has been particularly shown and described in conjunction with exemplary embodiments, it will be appreciated that variations and modifications will occur to those skilled in the art. Therefore, it is to be understood that the appended claims are intended to cover all such modifications and changes that fall within the true spirit of the invention.

What is claimed is:

1. A computer-implemented method comprising:
    capturing a current movement rate and biometric data for each user among a plurality of users performing a physical activity;
    predicting, based on the current movement rate and biometric data, an upcoming movement rate for each user; and
    generating, using a music generation system, music having an optimized beat based on a lowest upcoming movement rate among the predicted upcoming movement rates.

2. The computer-implemented method of claim 1, further comprising collecting historical activity data for a user and predicting the upcoming movement rate for the user using machine learning techniques based on the current movement rate, biometric data, and historical activity data of the user.

3. The computer-implemented method of claim 1, further comprising delivering the generated music to an output device.

4. The computer-implemented method of claim 1, wherein the current movement rate and biometric data are captured from at least one wearable internet of things (IoT) device worn by the user.

5. The computer-implemented method of claim 1, further comprising capturing one or more environmental factors related to the physical activity and predicting the upcoming movement rate for each user based on the captured environment factors.

6. The computer-implemented method of claim 1, further comprising generating the music having the optimized beat based on a preference of a user among the plurality of users.

7. The computer-implemented method of claim 1, further comprising predicting an upcoming movement rate of a first user based on a comparison of a physical attribute of the first user and a second user.

8. A system for dynamically generating music, comprising:
- a memory medium comprising program instructions;
- a bus coupled to the memory medium; and
- a processor, for executing the program instructions, coupled to a music generation engine via the bus that when executing the program instructions causes the system to:
- capture a current movement rate and biometric data for each user among a plurality of users performing a physical activity;
- predict, based on the current movement rate and biometric data, an upcoming movement rate for each user; and
- generate, using a music generation system, music having an optimized beat based on a lowest upcoming movement rate among the predicted upcoming movement rates.

9. The system of claim 8, the instructions further causing the system to collect historical activity data for a user and predicting the upcoming movement rate for the user using machine learning techniques based on the current movement rate, biometric data, and historical activity data of the user.

10. The system of claim 8, the instructions further causing the system to deliver the generated music to an output device.

11. The system of claim 8, wherein the current movement rate and biometric data are captured from at least one wearable internet of things (IoT) device worn by the user.

12. The system of claim 8, the instructions further causing the system to capture one or more environmental factors related to the physical activity and predicting the upcoming movement rate for each user based on the captured environment factors.

13. The system of claim 8, the instructions further causing the system to generate the music having the optimized beat based on a preference of a user among the plurality of users.

14. The system of claim 8, the instructions further causing the system to predict an upcoming movement rate of a first user based on a comparison of a physical attribute of the first user and a second user.

15. A computer program product embodied in a computer readable medium that, when executed by a computer device, performs a method for dynamically generating music, the method comprising:
- capturing a current movement rate and biometric data for each user among a plurality of users performing a physical activity;
- predicting, based on the current movement rate and biometric data, an upcoming movement rate for each user; and
- generating, using a music generation system, music having an optimized beat based on a lowest upcoming movement rate among the predicted upcoming movement rates.

16. The program product of claim 15, the method further comprising collecting historical activity data for a user and predicting the upcoming movement rate for the user using machine learning techniques based on the current movement rate, biometric data, and historical activity data of the user.

17. The program product of claim 15, the method further comprising delivering the generated music to an output device.

18. The program product of claim 15, wherein the current movement rate and biometric data are captured from at least one wearable internet of things (IoT) device worn by the user.

19. The program product of claim 15, the method further comprising capturing one or more environmental factors related to the physical activity and predicting the upcoming movement rate for each user based on the captured environment factors.

20. The program product of claim 15, the method further comprising generating the music having the optimized beat based on a preference of a user among the plurality of users.

* * * * *